US006190680B1

(12) United States Patent
Sakurada et al.

(10) Patent No.: US 6,190,680 B1
(45) Date of Patent: Feb. 20, 2001

(54) OILY COMPOSITION AND PROCESS FOR PRODUCING THE SAME

(75) Inventors: Satoshi Sakurada, Miura; Hisako Yoshino, Yokohama, both of (JP)

(73) Assignee: The Nisshin Oil Mills, Ltd., Tokyo (JP)

(*) Notice: Under 35 U.S.C. 154(b), the term of this patent shall be extended for 0 days.

(21) Appl. No.: 09/282,214

(22) Filed: Mar. 31, 1999

(30) Foreign Application Priority Data

| Apr. 1, 1998 | (JP) | 10-105418 |
| Apr. 1, 1998 | (JP) | 10-105419 |
| Apr. 1, 1998 | (JP) | 10-105420 |
| Sep. 24, 1998 | (JP) | 10-269222 |
| Sep. 24, 1998 | (JP) | 10-269223 |

(51) Int. Cl.$^7$ ............ A61K 9/107; A23F 3/30; A23L 1/222; B01F 3/12
(52) U.S. Cl. ............ 424/401; 424/94.1; 424/489; 426/650; 426/655; 514/938; 514/964; 514/974; 516/21; 516/22; 516/29; 516/31
(58) Field of Search ............ 516/21, 22, 29, 516/31; 514/938, 974; 424/401; 426/650, 655

(56) References Cited

U.S. PATENT DOCUMENTS

| 3,492,399 | * | 1/1970 | Prigal | 514/938 X |
| 4,013,475 | * | 3/1977 | Liebowitz et al. | 516/22 X |
| 4,844,934 | * | 7/1989 | Lueddecke et al. | 516/29 X |
| 4,874,605 | * | 10/1989 | Urban, Jr. et al. | 514/938 X |
| 5,015,469 | * | 5/1991 | Yoneyama et al. | 516/22 X |
| 5,039,559 | * | 8/1991 | Sang et al. | 516/22 X |
| 5,143,722 | * | 9/1992 | Hollenberg et al. | 424/401 X |
| 5,250,289 | * | 10/1993 | Boothroyd et al. | 514/938 X |
| 5,322,685 | * | 6/1994 | Nakagawa et al. | 514/938 X |
| 5,478,561 | * | 12/1995 | Ferrero | 424/401 |
| 5,603,863 | * | 2/1997 | Dahms | 516/22 X |
| 5,635,171 | * | 6/1997 | Nadaud | 514/938 X |

FOREIGN PATENT DOCUMENTS

| 63-135483 | 6/1988 | (JP) . |
| 4-64638 | 10/1992 | (JP) . |
| 6-343400 | 12/1994 | (JP) . |

* cited by examiner

*Primary Examiner*—Richard D. Lovering
(74) *Attorney, Agent, or Firm*—Burns, Doane, Swecker & Mathis, LLP

(57) ABSTRACT

An oily composition comprises a solid phase containing a water-soluble effective substance and/or a water-dispersible effective substance and an oil phase containing an oily component and an emulsifying agent having an HLB value of not more than 10, wherein the solid phase is dispersed in the oil phase in the form of a fine particulate state having an average particle size of not more than 5 μm and the water content or the aqueous alcohol solution content of the solid phase is not more than 30% by weight.

16 Claims, No Drawings

OILY COMPOSITION AND PROCESS FOR PRODUCING THE SAME

BACKGROUND OF THE INVENTION

1. Technical Field of the Invention

The present invention relates to an oily composition and a process for producing the composition. More particularly, the present invention pertains to an oily composition excellent in storage stability and a process for producing the composition. The oily composition of the present invention may be used in the fields of foods, feeds, cosmetics, medicines, agricultural chemicals, machines and other various industrial fields, because of its excellent storage stability.

2. Prior Art

A water-soluble effective substance and/or a water-dispersible effective substance (hereinafter referred to as "aqueous effective substance") may be dispersed in an oil by directly adding the aqueous effective substance to the oil containing an emulsifying agent dissolved therein and mixing them. However, this process does not permit easy preparation of any uniform and stable dispersion of such an aqueous effective substance in an oil phase and does not ensure any effect of masking the taste of the aqueous effective substance. This is because the dispersion prepared by the method entrains coagulation and/or precipitation of the effective substance. In general, there has widely been adopted a method comprising the step of mixing and emulsifying a solution of an aqueous effective substance in an aqueous phase with an oil phase to thus give a water-in-oil type emulsified composition. As such water-in-oil (or W/O) type emulsified compositions whose aqueous phase contains certain substances, there have been proposed, for instance, a W/O type emulsion containing an antioxidant hardly soluble in oils and fats or a synergist [Japanese Patent Publication for Opposition Purpose (hereinafter referred to as "J. P. KOKOKU") No. Hei 4-64638], a W/O type lipophilic antioxidant containing a water-soluble antioxidant substance emulsified therein [Japanese Patent Un-Examined Published Application (hereinafter referred to as "J. P. KOKAI") No. Sho 63-135483], and a W/O type emulsified composition containing an acidic substance and/or a salt thereof (J. P. KOKAI No. Hei 6-343400).

However, any W/O type emulsified composition has not yet been developed, which can sufficiently, satisfactorily be applied to various applications in the foregoing industrial fields because the foregoing W/O type emulsified composition does not undergo any separation immediately after the preparation, but the composition causes the separation of the aqueous phase or the oiling off phenomenon during storage thereof due to the action of salts and acidic substances coexisting in the aqueous phase. In addition, a large quantity of water is present in the aqueous phase and this becomes a cause of hygienic problems such as decomposition and/or putrefaction of the aqueous effective substances and the growth of mold. Moreover, the W/O type emulsion never ensures a sufficient effect of masking the taste of the aqueous effective substances.

PROBLEMS THAT THE INVENTION IS TO SOLVE

Accordingly, it is an object of the present invention to provide an oily composition which does not entrain any precipitation of aqueous effective substances, has excellent storage stability shows an effect of masking the taste of the aqueous effective substances, and is excellent in hygienic properties even when it is stored for a long time period, which can show a variety of functions such as an anti-oxidant action superior to that observed when the aqueous effective substance per se is used as an anti-oxidizing agent, and which can be used in combination with an oily antioxidant, as well as a method for preparing the composition.

MEANS FOR SOLVING THE PROBLEMS

The inventors of this invention have conducted various studies and have found that the foregoing objects of the invention can be accomplished by providing an oily composition wherein an aqueous effective substance, in a specific fine particulate state, is dispersed in an oil phase and the overall content of water in the composition is limited to a specific range.

The present invention has been completed on the basis of the foregoing finding and relates to an oily composition which comprises a solid phase containing a water-soluble effective substance and/or a water-dispersible effective substance and an oil phase containing an oily component and an emulsifying agent whose HLB value is not more than 10, wherein the foregoing solid phase is dispersed in the oil phase in a fine particulate state whose average particle size is not more than 5 $\mu$m and wherein the content of water or alcoholic aqueous solution present in the solid phase is not more than 30% by weight.

According to another aspect of the present invention, there is provided an oily composition which comprises a solid phase containing a water-soluble effective substance and/or a water-dispersible effective substance and a water-soluble film-forming agent in an amount ranging from 1 to 2000 parts by weight per 100 parts by weight of the sum of the water-soluble effective substance and/or the water-dispersible effective substance; and an oil phase containing an oily component and an emulsifying agent whose HLB value is not more than 10, wherein the foregoing solid phase is dispersed in the oil phase in a fine particulate state whose average particle size is not more than 5 $\mu$m and wherein the content of water present in the solid phase is not more than 30% by weight.

According to a still another aspect of the present invention, there is provided a process for preparing an oily composition which comprises the steps of emulsifying an aqueous phase containing a water-soluble effective substance and/or a water-dispersible effective substance, a water-soluble film-forming agent and water or an aqueous alcohol solution with an oil phase containing an oily component and an emulsifying agent to give a W/O type emulsion and then drying the resulting emulsion.

MODE FOR CARRYING OUT THE INVENTION

The oily composition of the present invention will first be described in detail below.

The oily composition of the present invention comprises a solid phase containing an aqueous effective substance and an oil phase containing an oil component and an emulsifying agent having an HLB value of not more than 10.

The aqueous effective substance used in the present invention is not restricted to any specific one and may be any substance soluble in water and dispersible in water, with those soluble in water or an aqueous alcohol solution being preferred. The term "aqueous alcohol solution" used above means a mixed solution of water and an alcohol, for instance, a solution obtained by dissolving 1 to 300 parts by weight of a primary alcohol such as ethanol or methanol in 100 parts by weight of water.

The method for preparing the foregoing aqueous effective substance is not also restricted to any specific one and those prepared by a variety of methods may be used in the invention without any restriction.

The aqueous effective substance may be, for instance, drugs, vaccines and extracts of animals and plants such as coloring agent, enzymes, bacteria, antioxidants, physiologically active substances, preservatives, bitter agents, acidulants, flavoring agents, anti-oxidizing agents, seasonings, inorganic salts, starch, starch hydrolyzates, peptides, polypeptides possessing physiological activity, amino acids, dietary fibers, celluloses, nutrient enrichment agents, crude drug extracts, drugs for treating diabetes, antipyretics, anti-inflammatory agents, analgesics, sedatives, antiallergic agents, antibiotics, antiulcerous agents, antitumour agents, anticoagulants, antihemorrhagics, cardiacs, muscle relaxants, anesthetics, antiarrhythmic agents and vasodilators. Specific examples thereof includes citric acid and salts thereof, phosphoric acid and salts thereof, metaphosphoric acid and salts thereof, gardenian blue color, caramel, cacao pigment, grape skin color, strawberry color, shisonin color, phospholipase, amylase, dehydrogenase, Takadiastase N1, lactic acid bacteria, butyric acid bacteria, bifidus bacteria, nucleic acids, yeast, taurine, common salt, soy sauce, sodium carbonate, sodium citrate, corn starch, dextlin, milk peptides, corn peptides, insulin, somatostatin, thyroid stimulating hormones, parathyroid hormones, growth hormones, luteinizing hormone-release hormones, L-tryptophane, lysine chloride, sodium glutamate, sodium aspartate, polydextrose, microcrystalline cellulose, ascorbic acid and salts thereof, nicotinamide, nicotinic acid, magnesium L-ascorbyl phosphate, vitamin B's, niacin, calcium pantothenate, folic acid, biotin, calcium salts such as calcium chloride, milk minerals, calcium lactate, casein-calcium-peptide (CCP), casein phosphopeptide (CPP), Calcium Saitoremato (CCM), beef bone meal, shell powder, heme iron, zinc, arbutin, kojic acid, Nifedipine, Ubidecarenone, Nicardipine, Methotrexate, Somatostatin, Phenformin HCl, Glipizide, Buformin HCl, Glymidine Sodium, sodium salicylate, Sodium Flufenamate, Sulpyrine, Prochlorperazine, Chlorpromazine HCl, Diphenhydramine HCl, Methdilazine HCl, Chlorpheniramine Maleate, Amikacin, Tobramycin, Lividomycin, Gentamicin, Kanendomycin, Tetracycline HCl, Dibekacin, Ampicillin, Metoclopromide, Mitomycin C, Bleomycin HCl, Actinomycin D, Methotrexate, Daunorubicin HCl, Vinclistine Sulfate, Vinblastine Sulfate, Adriamycin, Lentinan, Glycyrrhizin, Heparin Sodium, Thrombin, Thromboblastine, Transbioxo camphor, Aminophylline, Theophyllol, Piridinol Methanesulfonate, Tubocurarine Chloride, Bufetolol HCl, Diltiazem HCl, Oxyfedone HCl, dipotassium glycyrrhizate, Chlorpheniramine Maleate, codeine phosphate, Aspirin, acetoaminophenone, Chlorpheniramine d-Maleate, Tipepidine Hibenzoate, Bisbentiamine, magnesium metasilicate aluminate, Carbetapentane Citrate, Potassium Guaiacolsulfonate, influenza vaccine, gymnema, gymnema sylvestre extract, Job's tears extract, honey, royal jelly, propolis, RAKANKA extract, herb extracts, grape extract, blueberry extract, blueberry leaf extract, rosemary extract, tea extract, catechin, TOCHU extract, scopolia extract, Pollen, naringin, spice extracts, cowberry extract, caffeine, Phellodendion Powder, iodine, cobalt, selenium, oligosaccharides, xylooligosaccharides, garlic extract, shiitake extract, wasabi (Japanese horseradish), polygonum, pine needle extract, basil, coca, Japanese pepper, perilla, perilla extract, mustard, rice bran-enzyme decomposition products, chlorella, taurine, Supirullina, Ezo Araliaceae, chitin, chitosan, rutin, safflower extract, raw coffee bean extract, sunflower seed extract, aloe, iso-α-bitter acid, gentian extract, Fomes japonicus and extract thereof, plant worm extract, mamushi extract, MAROU extract, snapping turtle extract, oyster extract, magwort extract, lycii fructus, lycii cortex, Sasa albo-marginata extract, ginseng extract, DENSHICHI NINJIN extract, gingko leaf extract, carrot leaf extract, octacosanol, herbaceous peony, corydalis decumbens Persoon, RYOKYO, Amomum xanthioides Wall., Borei, corydalis decumbens Persoon, cinnamon extract, bitter orange extract, Japanese persimmon extract, Kudzu flower extract, Foeniculum vulgare Mill. extract, ginger extract, Ezo Araliaceae extract, hawthorn extract, guarana extract, OSEI extract, yellow day lily extract, isoleucine, threonine, phenylalanine, naringin, niacinamide, lysine, threonine, arginine, guarana, oyster meat extract, gymnema sylvestre extract, reindeer horn extract, stevia, deep-sea shark extract, sea bear extract, milt proteins, and placenta extract.

The foregoing aqueous effective substances may be used alone or in any combination of at least two thereof. In addition, the content of the aqueous effective substance preferably ranges from 60 to 100% by weight and more preferably 70 to 100% by weight on the basis of the total weight of the solid phase of the oily composition of the present invention.

The solid phase of the oily composition of the present invention is water which comprises the foregoing aqueous effective substance. The water used in the invention is not particularly restricted and may be purified water, distilled water, tap water and pH-adjusted water. Moreover, it is also possible to use aqueous alcohol solutions obtained by adding alcohols to the foregoing water. The aqueous alcohol solution means a mixed solution comprising water and an alcohol and specific examples thereof include those obtained by dissolving 1 to 300 parts by weight of a primary alcohol such as ethanol or methanol in 100 parts by weight of water.

The oily composition of the present invention may comprise a polyhydric alcohol. Various kinds of polyhydric alcohols may be used in the invention and preferably used in the invention are water-soluble polyhydric alcohols each having, in the molecule, preferably at least two, more preferably 2 to 12 and most preferably 2 to 6 hydroxyl groups. Examples of such polyhydric alcohols are glucose, maltose, maltitol, sorbitan, sorbitol, sucrose, lactose, fructose, xylitol, inositol, erythritol, pentaerythliitol, propylene glycol, 1,3-butylene glycol, ethylene glycol, glycerin, diglycerin, polyglycelin (average degree of polymerization: 4 to 10), sacchaiified products of reduced starch, glucose/fructose liquid sugar and fructose/glucose liquid sugar. The foregoing polyhydric alcohols may be used alone or in any combination. If the foregoing polyhydiic alcohol is incorporated into the oily composition of the present invention, the resulting composition is further improved in its long-term storage stability and freezing resistance.

The content of the foregoing polyhydric alcohol preferably ranges from 1 to 40% by weight, more preferably 5 to 40% by weight and most preferably 10 to 40% by weight on the basis of the total weight of the solid phase of the oily composition.

An emulsifying agent having an HLB value of not less than 10 may, if necessary, be incorporated into the solid phase of the oily composition of the invention. The HLB value of the emulsifying agent used herein is preferably not more than 20. Examples of such emulsifying agents whose HLB value is not less than 10 include sucrose fatty acid esters, polyglycerin fatty acid esters, extracted lecithin, enzyme-decomposed lecithin, hydrogenated lecithin, saponin, glycolipids, proteins, protein hydrolyzates (other than gelatin and glue), silicone type emulsifying agents and alkylene oxide-added emulsifying agents. When adding an emulsifying agent having an HLB value of not less than 10 to the composition, the content thereof in the composition preferably ranges from 0.01 to 5% by weight on the basis of the total weight of the composition.

Moreover, the solid phase of the oily composition of the invention may likewise comprise an additive selected from known antiseptics, coloring agents, flavoring agents and pH-adjusting agents. If such an additive is incorporated, the content thereof in the composition preferably ranges from 0.01 to 5% by weight on the basis of the total amount of the solid phase of the composition.

The solid phase of the oily composition of the invention is dispersed in, an oil phase as will be detailed later, the form of fine particles having an average particle size of not more than 5 $\mu$m. The average particle size of the solid phase is preferably not more than 3 $\mu$m and more preferably 0.05 to 2 $\mu$m. This is because if the average particle size thereof exceeds 5 $\mu$m, the storage stability of the resulting oily composition is considerably reduced.

The method for dispersing, in the oil phase, the solid phase in the form of fine particles having an average particle size of not more than 5 $\mu$m is not restricted to any particular one, but such a dispersed condition may be obtained by, for instance, gradually admixing the oil phase and the aqueous phase using a homomixer over about 30 minutes to thus uniformly mix and emulsify them, or treating the oil and solid phases in an emulsifier such as a high-pressure homogenizer or a microfluidizer, to thus finally obtain a W/O type emulsified product and then drying the emulsified product. In this respect, the term "finally obtain a W/O type emulsified product" means that the emulsion formed may be a W/O type or O/W type one or a mixture of O/W and W/O type ones at the initial stage of the emulsification, but the emulsion ultimately formed should be a W/O type one.

Incidentally, the term "the average particle size of the solid phase" herein used means a value determined using a laser diffraction type particle size distribution meter (LA-500 Type, available from Horiba, Ltd.).

The oil phase of the oily composition of the invention will now be described below in detail. The oil phase comprises an emulsifying agent and an oil component. The emulsifying agent is not restricted to any specific ones and may be, for instance, any known emulsifying agents used in the fields of, for instance, foods, feeds, cosmetics, medicines and other industries. The emulsifying agent used in the present invention has an HLB value of not more than 10. In addition, it is preferred to use an emulsifying agent having an HLB value of not less than 1. This is because if only emulsifying agents each having an HLB value of higher than 10 is used, it is difficult or impossible to obtain a composition comprising solid particulate phase having an average particle size of not more than 5 $\mu$m.

Examples of emulsifying agents each having an HLB value of not more than 10 include sorbitan fatty acid esters, glycerin fatty acid esters, organic acid monoglycerides, propylene glycol fatty acid esters, diglycerides, sucrose fatty acid esters, polyglycerin fatty acid esters, hydrogenated lecithin, lecithin, silicone type emulsifying agents and alkylene oxide-added surfactants. Specific examples thereof include sorbitan monooleate, sorbitan distearate, polyoxyethylene (6 moles) sorbitan monostearate, glycerin monostearate, glycerin monolinolate, esters of citric acid and glycerin monooleate, propylene glycol monostearate, glycerin dioleate, glycerin dilinolate, diglycerides obtained through transesterification of rape seed oil and glycerin, diglycerides obtained through transesterification of safflower oil and glycerin, diglycerin distearate, diglycelin tristearate, hexaglycerin trioleate, hexaglycerin pentastearate, tetraglycerin-condensed ricinolate, polyglycerin-condensed licinoleic acid ester, sucrose tri- to pentastearates, polyoxyethylene (5 moles) cetyl ether, polyoxyethylene (3 moles) nonylphenyl ether, polyoxyethylene (6 moles) stearyl ether, polyoxyethylene (5 moles) hardened castor oil, polyoxyethylene (15 moles) hardened castor oil, polyoxyethylene (20 moles) sorbitol tetraoleate, lecithin (Lecithin DX BASIS LP-20; available from The Nissin Oil Mills, Ltd.), hydrogenated lecithin (BASIS LP-20H; available from The Nissin Oil Mills, Ltd.), dimethylsiloxane-methyl(polyoxyethylene (5 moles))siloxane copolymer and dimethylsiloxane-methyl(polyoxyethylene(5 moles)) siloxane-methyl(polyoxy propylene (5 moles)) siloxane copolymer.

In the present invention, the foregoing emulsifying agents may be used alone or in any combination of at least two of them.

In the present invention, it is also possible to use a combination of an emulsifying agent having an HLB value of not more than 10 and another emulsifying agent having an HLB value of not less than 10. Examples of such emulsifying agents are sucrose fatty acid esters, polyglycerin fatty acid esters, extracted lecithin, enzyme-decomposed lecithin, hydrogenated lecithin, saponin, glycolipids, proteins, protein hydrolyzates (other than gelatin and glue), silicone type surfactants and alkylene oxide-added surfactants. Specific examples thereof include sucrose stearic acid monoesters, hexaglycerin oleic acid monoesters, decaglycerin stearic acid monoesters, extracted lecithin (BASIS LS-60 available from The Nissin Oil Mills. Ltd.), enzyme-decomposed lecithin (BASIS LG-10OK, BASIS LP-20E available from The Nissin Oil Mills. Ltd.), hydrogenated lecithin (BASIS LS-60H available from The Nissin Oil Mills. Ltd.), quillaia saponin, soybean protein hydrolyzates, sodium caseinalte, wheat gluten hydrolyzates, dimethylsiloxane-methyl (polyoxyethylene(60 mole))siloxane copolymers, polyoxyethylene(25 moles)hardened castor oil and polyoxyethylene(80 moles)hardened castor oil. It is particularly desirable in the present invention to use polyglycerin-condensed ricinoleate alone or in combination with polyglycerin fatty acid esters or glycerin fatty acid monoester or lecithin.

In the present invention, the emulsifying agents each having an HLB value of not less than 10 may be used alone or in any combination of at least two of them.

The foregoing oily component herein used may be any known ones used in the fields of foods, feeds, cosmetics, medicines and other industries, without any particular restriction. As the oily component, herein used are those in the liquid state. Moreover, the oily component may be those in the liquid state at ordinary temperature and it may be those in the solid state, inasmuch as they can be molten by heating. The oily component may be, for instance, hydrocarbons, esters, animal and vegetable oils and fats, waxes, goby oils, higher fatty acids, higher alcohols, silicone type substances, sterols, and resins as well as those obtained by enzymatically (for instance, hydrolysis and transesterification) or chemically (for instance, transesterification and hydrogenation) treating the foregoing substances.

Specific examples thereof include soybean oil, rape seed oil, corn oil, sesame oil, cotton seed oil, safflower oil, sunflower oil, peanut oil, rice germ oil, wheat germ oil, husked rice germ oil, Job's tears oil, macadamia nut oil, garlic oil, camellia oil, palm oil, olive oil, jojoba oil, macadamia nut oil, avocado oil, castor oil, linseed oil, beefsteak plant oil, eucalyptus oil, evening primrose oil, turtle oil, mink oil, lard, beef tallow, equine oil, snake oil, fish oil, egg oil, egg yolk oil, liquid paraffin, isoparaffin, vaseline, squalane, squalene, turpentine oil, isopropyl myristate, isopalmityl myristate, 2-octyldodecyl myristate, cetyl 2-ethylhexanoate, glyceryl tri-2-ethylhexanoate, glyceryl tricaprylate, triglycerides of mixed fatty acids of caprylic and capric acids, neopentyl glycol di-2-ethylhexanoate, diisostearyl malate, isononyl isononanoate (3,5,5-trimethylhexyl-3',5',5'-trimethyl-hexanoate), cholesteryl 12-hydroxystearate, monoesters to hexaesters of dipentaerythritol and isostearic acid and/or higher fatty acids available from Emery Co., Ltd., glyceryl esters of p-methoxycinnamic acid and 2-ethylhexanoic acid, and isooctyl p-methoxycinnamate.

Specific examples of the oily components further include hardened soybean oil, hardened rape seed oil, hardened palm oil, hardened fish oil, glyceryl tristearate, rosin, cholesterol, phytosterols (such as campesterol, stigmasterol and sitosterol), orange raffinate, lanolin, myristic acid, palmitic acid, isopalmitic acid, stearic acid, isostearic acid available from Emery Co., Ltd., oleic acid, linolic acid, linoleic acid, ricinoleic acid, 12-hydroxystearic acid, 10-hydroxystearic acid, behenic acid, erucic acid, arachidonic acid, eicosapentaenoic acid, docosahexaenoic acid, myristyl alcohol, cetyl alcohol, stearyl alcohol, isostearyl alcohol, behenyl alcohol, lanolin alcohol, paraffin waxes, microcrystalline waxes, ceresine waxes, bees wax, vaseline, hard fats, carnauba wax, candelilla wax, rice wax, rice bran wax, Japan wax, shellac, dimethylpolysiloxane, methylphenylpolysiloxane and essential oils derived from animals and vegetables. These oily components may be used alone or in any combination of at least two of them.

The content of the oily component in the oil phase of the oily composition according to the present invention preferably ranges from 0.5 to 50% by weight and more preferably 1 to 30% by weight. The oil phase is preferably in a liquid or paste-like state at ordinary temperature from the viewpoint of the ability of producing and handling the composition. The oily composition prepared using an oil phase that is in a liquid or paste-like state at ordinary temperature is in a liquid or paste-like state at ordinary temperature.

The oil phase of the oily composition of the invention may further comprise known additives such as antiseptics, colorants and flavors. When the oily composition comprises such additives, the amount thereof to be added preferably ranges from 0.01 to 5% by weight based on the total amount of the oil phase of the composition.

The oily composition of the present invention may contain an oil-soluble effective substance in the oil phase. The oil-soluble effective substance may be, for instance, antioxidants, nutrient supplements, drugs and animal and plant extracts and specific examples thereof include mixed tocopherols, dl-α-tocopherol, acetic acid-dl-α-tocopherol, tocotrienol, EPA, DHA, sesame oil extract, β-carotene, vitamin A, rosemary oil, vitamin D's, vitamin K's, essential fatty acids, rice bran oil extract, γ-oryzanol, extract of swertiae herba, propolis extract, sage extract, pepper extract, squalene, snapping turtle oil and cod liver oil. These oil-soluble effective substances may be used alone or in any combination of at least two of them.

When the oil phase comprises the oil-soluble effective substance, the content thereof in the oil phase preferably ranges from 0.1 to 99% by weight and more preferably 0.2 to 40% by weight on the basis of the total weight of the oil phase.

The oily composition of the present invention preferably comprises 5 to 75% by weight of the foregoing solid phase and 95 to 25% by weight of the foregoing oil phase.

The solid phase of the oily composition of the invention has a water content or an aqueous alcohol solution content of not more than 30% by weight, preferably not more than 20% by weight, more preferably not more than 10% by weight and most preferably not more than 5% by weight. This is because if the water or aqueous alcohol solution content in the solid phase is more than 30% by weight, the storage stability of the resulting oily composition is extremely reduced and this in turn results in the deterioration of the aqueous effective substance and the growth of mold in the oily composition.

The method for adjusting the water or aqueous alcohol solution content in the solid phase of the oily composition to not more than 30% by weight is not restricted to any specific one, but this may be accomplished by such a method as drying under reduced pressure, drying with heating, drying with a thin film evaporator and freeze-drying.

The method for preparing the oily composition of the present invention is not restricted to any specific one, but the composition may be prepared by, for instance a method detailed below.

A second embodiment of the oily composition of the present invention will now be described in detail below.

The oily composition of the present invention comprises a solid phase which comprises an aqueous effective substance and a water-soluble film-forming agent in an amount ranging from 1 to 2000 parts by weight per 100 parts by weight of the aqueous effective substance; and an oil phase which comprises an oily component and an emulsifying agent having an HLB value of not more than 10.

The oily composition according to the second embodiment of the present invention is the same as that discussed above, provided that the solid phase comprises a water-soluble film-forming agent in addition to the foregoing components. Therefore, the components other than the film-forming agent and the contents thereof are the same as those discussed above.

The term "water-soluble film-forming agent" used above means a substance capable of forming a film when an aqueous solution thereof is dried and examples thereof include gelatin, gum arabic, glue, microorganism cultivation-starch product, hemicellulose and water-soluble film-forming synthetic polymers.

The term "gelatin" herein used means polypeptides obtained by subjecting collagen contained in bones and/or skins of animals in a large amount to a series of steps such as decomposition, extraction, purification and drying. Gelatin herein used is not restricted to any particular one and may be those commonly used in the fields of foods, feeds, cosmetics, medicines and other industries. Moreover, also usable herein include, for instance, purified gelatin obtained by subjecting the foregoing gelatin to an additional treatment such as bleaching and purification.

The term "gum arabic" used herein means those commonly used in the fields of foods, feeds, cosmetics, medicines and other industries.

The term "glue" herein used means gelatin having a high content of impurities or those commonly used in the fields of foods, feeds, cosmetics, medicines and other industries.

The term "microorganism cultivation-starch products" herein used means neutral polysaccharides prepared by culturing microorganisms on a starch medium and then subjecting the culture medium to a series of treatments including, for instance, extraction, purification and drying steps and may be, for instance, those commonly used in the fields of foods, feeds, cosmetics, medicines and other industries. Specific examples thereof include pullulan.

The term "hemicellulose" used in the invention means water-soluble polysaccharides extracted and/or purified from broad-leaved trees, needle-leaved trees, true grasses, seeds and husks of seeds, or those obtained by further hydrolyzing them, for instance, subjecting them to a chemical treatment with, for instance, an acid or an alkali; to a physical treatment using, for instance, heat or pressure; or to a biological treatment with, for instance, an enzyme. The foregoing hemicellulose may be those commonly used in the fields of foods, feeds, cosmetics, medicines and other industrial fields. Examples of such hemicellulose are arabinogalactan extracted and purified from trees belonging to the genus Japanese larch, corn fibers extracted and purified from husks of corn seeds (for instance, Cellace #40 available from Nippon Shokuhin Kako Co., Ltd.), fibers extracted and purified from soybean (such as Soyafibe-S available from Fuji Oil Co., Ltd.), and xylan derived from wheat flour.

Examples of the water-soluble film-forming synthetic polymers usable in the present invention are carboxymethyl cellulose, methyl cellulose, cellulose acetate phthalate, sodium polyacrylate, polyvinyl alcohol, polyvinyl pyrrolidone, polyvinyl methyl ether, carboxyvinyl polymers, hydroxyethyl cellulose, hydroxypropylmethyl cellulose, CARBOPOL and poly(methyl vinyl ether/maleic anhydride), which have commonly been used in the fields of, for instance, cosmetics, medicines and other industrial fields.

In the present invention, the water-soluble film-forming agents may be used alone or in any combination of at least two of them.

The amount of the water-soluble film-forming agent to be used ranges from 1 to 2000 parts by weight per 100 parts by weight of the foregoing aqueous effective substance. The amount of the film-forming agent is preferably in the range of from 1. to 1000 parts by weight per 100 parts by weight of the foregoing aqueous effective substance. Moreover, when gelatin or gum arabic is used as the water-soluble film-forming agent, it is preferably used in an amount ranging from 1 to 50 parts by weight and more preferably 1 to 40 parts by weight per 100 parts by weight of the foregoing aqueous effective substance.

The method for preparing the oily composition according to the second embodiment of the present invention is not restricted to any specific one, but the composition may be prepared by, for instance, the method described below.

The oily composition of the present invention can be used in, for instance, foods, feeds, cosmetics, industrial products and medicines without any pre-treatment or after diluting it with an oily component or an organic solvent such as ethanol or xylene. In this respect, when the oily composition is diluted with an oily component or an organic solvent, the dilution factor with respect to the amount of the oily composition (which is defined to be 1) preferably ranges from 0.01 to 10000 and more preferably 0.1 to 1000. If the oily component used for the dilution is, for instance, a hardened oil or a wax which is in a solid state at ordinary temperature, the oily composition of the present invention may be obtained in the form of a solid, a granule or powder, even when the former is in a liquid state. Alternatively, the oily composition of the present invention may be converted into a solid, granular or powdery state by incorporating, in advance, a solid fat, a hardened oil or a wax into the oily component of the composition.

The oily composition of the present invention may be used in a variety of products, for instance, noodles such as Chinese noodles, Chinese noodles served with frizzled vegetables, wheat vermicelli, buckwheat vermicelli, macaroni, spaghetti, fried noodles and non-fried noodles; powdery and liquid soups; sauces; dairy products such as yoghurt, formulated milk, powdered milk for infants, ice cream, yoghurt, cream and whipped cream; confectionery such as rice crackers, snacks, biscuits, wafers, chocolates, wheat gluten, caramels, chewing gum, candies and Gumi; marine paste products such as tube-shaped fish paste, fish cake, fish sausage and fish ham; frozen foods such as frozen tempura, frozen fried foods without coat, frozen flied foods, frozen raw dumpling stuffed with minced pork and frozen shao-mai; foods such as miso, hamburger steak, ham, sausage, fried dumpling stuffed with minced pork, shao-mai, bread, edible oils, butter, margarine, shortening oils, cheese, mayonnaise, dressings, drinks, health foods, and diets; cosmetics such as lip colors, cosmetic creams, milky lotions, shampoo, products for rinse, agents for pack and poultices; medicines and quasi-drugs such as nutrient supplement drinks, powdery drugs, tablets, ointments and vitamin preparations; industrial products such as fertilizers and lubricating agents; and other industrial products such as feeds.

Moreover, when a person eats the oily composition of the present invention to which an aqueous effective substance having a taste such as sourness, bitterness or astringency is added, the person is scarcely conscious of such a taste of the substance. Accordingly, the oily composition of the present invention permits the masking of the taste of such an aqueous effective substance if the composition is incorporated into, for instance, foods and medicines.

The oily composition of the present invention can be used in the form of capsules by encapsulating it in any known capsule (such as a gelatin capsule or agar capsule).

Moreover, the aqueous effective substance and the oily effective substance have conventionally been added separately to foods, feeds, cosmetics, industrial products and medicines, but the oily composition of the present invention permits the simultaneous use of these aqueous effective and oily effective substances.

In addition, a product in which an aqueous effective substance is uniformly and finely dispersed in an oily substance can easily be prepared by the addition of the oily composition of the present invention to the oily substance such as an oil or fats and oils. Moreover, the oily composition of the present invention never causes any release of water and any separation of the aqueous effective substance from the composition during the storage thereof, unlike the water-in-oil type emulsion whose aqueous phase contains a large quantity of water. Moreover, the aqueous effective substance does not exposed to the outside air in the composition of the present invention and accordingly, the composition can inhibits any deterioration, decomposition, putrefaction or the like of the aqueous effective substance per se.

In addition, the oily composition shows an effect of sustained release of the aqueous effective substance. For instance, a fertilizer having a delayed action may be prepared by incorporating the oily composition into the fertilizer. Alternatively, if the oily composition is incorporated into a chewing gum, the resulting chewing gum can release its taste in the mouth over a long time period.

The method for preparing the oily composition of the present invention will now be described in more detail below.

The method for preparing the oily composition of the present invention comprises the steps of emulsifying an aqueous phase which comprises a water-soluble effective substance and/or a water-dispersible effective substance, a water-soluble film-forming agent and water or an aqueous alcohol solution with an oil phase containing an oily component and an emulsifying agent to give a W/O type emulsion and then drying the resulting emulsion.

The water-soluble effective substance and/or the water-dispersible effective substance, the water-soluble film-forming agent, the water or the aqueous alcohol solution, the oily component and the emulsifying agent each may be the same as those included in the oily composition of the present invention.

In the method for preparing the oily composition of the present invention, an aqueous phase is first prepared by mixing water with an aqueous effective substance, a water-soluble film-forming agent and water or an aqueous alcohol solution. The aqueous phase may further comprise, for instance, a polyhydric alcohol and a thickening stabilizer. In addition, the aqueous phase may also comprise additives, which can be added to the solid phase of the oily composition of the present invention.

Then the foregoing aqueous phase is heated to a temperature ranging from 10 to 90° C. to thus convert the aqueous phase into a solution. When an aqueous alcohol solution is used in the preparation of the aqueous phase, the temperature for heating the aqueous phase desirably ranges from 10 to 65° C.

Separately, an oily component and an emulsifying agent are admixed together to give an oil phase. The rate of the emulsifying agent in the oil phase preferably ranges from 0.5 to 50% by weight and more preferably 1 to 30% by weight based on the total weight of the oil phase. The oil phase may optionally comprise, for instance, an oily effective substance and other additives, which may be added to the oil phase of the oily composition of the invention.

Then the oil phase and the aqueous phase are admixed together to finally give a W/O type emulsion. In this case, the oil phase is also preferably heated to a temperature ranging from 10 to 90° C. Such heating of the oil phase permits the addition of an oily component, which is in the solid state at ordinary temperature. In this respect, the mixing ratio of the aqueous phase to the oil phase (the aqueous phase (part by weight)/the oil phase (part by weight) preferably ranges from 95/5 to 1/99 and more preferably 85/15 to 20/80.

The method usable herein for finally converting the mixture of the aqueous phase and the oil phase into the W/O type emulsion is not restricted to any specific one and may be any known one, for instance, a method in which the mixture of the aqueous and oil phases is emulsified using an emulsifier such as a propeller mixer, homomixer, homodisper, high pressure homogenizer or microfluidizer.

Then the W/O type emulsion thus prepared is subjected to a drying treatment to give an oily composition of the present invention. The drying treatment is carried out to such an extent that the water content or the aqueous alcohol solution content in the solid phase is preferably not more than 30% by weight, more preferably not more than 20% by weight, still more preferably not more than 10% by weight and most preferably not more than 5% by weight.

The method for drying the foregoing W/O type emulsion is not restricted to any particular one, but may, for instance, be drying under reduced pressure, drying with heating, drying with a thin film evaporator and freeze-drying. Moreover, the drying procedures may be carried out while the W/O type emulsion is still in a heated condition or after the emulsion is cooled to a temperature ranging from a freezing temperature to room temperature.

EXAMPLES

The present invention will hereinafter be described in more specifically with reference to the following Examples, but the present invention is not restricted to these specific Examples at all.

The following are methods for determining or calculating the water contents or the aqueous alcohol solution contents in an oily composition and the solid phase of the composition, the aqueous effective substance content in the solid phase, the amount of the water-soluble film-forming agent per 100 parts by weight of the aqueous effective substance, the content of the water-soluble film-forming agent in the solid phase, the polyhydric alcohol content in the solid phase and the average particle size of the solid phase, in the following Examples.

[Water Content or Aqueous Alcohol Solution Content in Oily Composition]

The water content in each oily composition was determined by the loss in weight on drying-method and the Karl-Fisher method, while the aqueous alcohol solution content was determined by the loss in weight on drying-method.

[Water Content or Aqueous Alcohol Solution Content in Solid Phase]

The water content and the aqueous alcohol solution content in the solid phase of each oily composition were calculated from the water content and the aqueous alcohol solution content in the oily composition according to the following equation, on such an assumption that all of the water or the aqueous alcohol solution present in the oily composition was contained in the solid phase:

Water or Aqueous Alcohol Solution Content in Solid Phase (% by weight)=[(Weight of Water or Aqueous Alcohol Solution in Oily Composition)/(Weight of Water or Aqueous Alcohol Solution in Oily Composition+Weight of Solid Phase Except for Water or Aqueous Alcohol Solution)]×100

[Content of Aqueous Effective Substance in Solid Phase]

Content of Aqueous Effective Substance in Solid Phase(% by weight)=[(Weight of Aqueous Effective Substance)/(Weight of Water or Aqueous Alcohol Solution in Oily Composition+Weight of Solid Phase Except for Water or Aqueous Alcohol Solution)]×100

[Amount of Water-Soluble Film-Forming Agent per 100 parts by weight of Aqueous Effective Substance]

Amount of Water-Soluble Film-Forming Agent per 100 parts by weight of Aqueous Effective Substance (part by weight)=(Weight of Water-Soluble Film-Forming Agent/Weight of Aqueous Effective Substance)×100

[Content of Water-Soluble Film-Forming Agent in Solid Phase]

Content of Water-Soluble Film-Forming Agent in Solid Phase (% by weight)=[(Weight of Water-Soluble Film- Forming Agent)/(Weight of Water or Aqueous Alcohol Solution in Oily Composition+Weight of Solid Phase Except for Water or Aqueous Alcohol Solution)]×100

[Polyhydric Alcohol Content in Solid Phase]

Polyhydric Alcohol Content in Solid Phase (% by weight)=[(Weight of Polyhydric Alcohol (Solid Content))/(Weight of Water or Aqueous Alcohol Solution in Oily Composition+Weight of Solid Phase Except for Water or Aqueous Alcohol Solution)]×100

[Average Particle Size of Solid Phase]

The average particle size of the solid phase present in each oily composition was determined using a laser diffraction type particle size distribution-determining device (LA-500 Type, available from Horiba Co., Ltd.).

Example 1

An aqueous phase was prepared by mixing 50.0 g of a grape seed extract with 400.0 g of water and then warming the mixture to 60° C. and separately, an oil phase was prepared by mixing 500.0 g of soybean oil with 50.0 g of tetraglycerin condensed ricinoleate (POEMU PR-100, HLB: 0.3 available from Riken Vitamin Co., Ltd.) and then heated to 60° C. to thus dissolve the emulsifying agent. To the oil phase, there was slowly added the foregoing aqueous phase while they were mixed together in a homomixer at 6000 rpm and 60° C. for 20 minutes to give an emulsion, followed by drying the emulsion using an oil pump to thus give a liquid brown oily composition containing grape seed extract. The water content of the oily composition was found to be 0.2% by weight. The water content and the grape seed extract content of the solid phase dispersed in the oil phase were found to be 2.4% by weight and 97.7% by weight, respectively. The average particle size of the solid phase was determined to be 0.4 μm. The resulting oily composition was inspected for the storage stability according to the following method. The evaluation results thus obtained are listed in Table 1 given below.

The resulting oily composition (1g) was mixed with 99 g of soybean oil to give white diluted oil of the oily composition.

[Storage Stability of Oily Composition]

The resulting oily composition was put in a thermostatic oven maintained at 5° C. or 40° C., followed by allowing it in the oven over 1, 3 and 6 months and then the appearance of the oily composition was visually observed. Separately, the oily composition was allowed to stand at room temperature for 1, 3 and 6 months and thereafter the appearance of the oily composition was also visually observed. The visual observation of the appearance was evaluated on the following criteria. The following Table also shows the results of the visual observation immediately after the preparation thereof.

◎: The oily composition did not show any abnormality at all.

○: There was observed the oil phase separation in an amount of less than 1% of the total volume of the composition.

Δ: There was observed the oil phase separation in an amount ranging from 1 to 5% of the total volume of the composition.

▲: There was observed the oil phase separation in an amount of not less than 5% of the total volume of the composition.

□: There was observed the solid phase (or aqueous phase) separation in an amount of less than 1% of the total volume of the composition.

■: There was observed the solid phase (or aqueous phase) separation in an amount of not less than 1% of the total volume of the composition.

X: There was observed the growth of mold.

Example 2

There were mixed 100.0 g of a blueberry extract, 40.0 g of glycerin and 350.0 g of a 25% by weight aqueous ethanol solution, followed by heating the mixture to 60° C. to give an aqueous phase, while 450.0 g of soybean oil, 30.0 g of tocopherol (Tocopherol 100 available from The Nissin Oil Mills, Ltd.) and 30.0 g of POEMU PR-100, followed by heating the mixture at 60° C. to give an oil phase. Subsequently, the same procedures used in Example 1 were repeated to give a liquid blueberry extract-containing oily composition of dark blue color. The aqueous ethanol solution content of the oily composition was found to be 0.1% by weight. The aqueous ethanol solution content, the blueberry extract content and the glycerin content of the solid phase dispersed in the oil phase were found to be 0.5% by weight, 71.1% by weight and 28.4% by weight, respectively. The average particle size of the solid phase was determined to be 0.6 μm. The resulting oily composition was inspected for the storage stability according to the procedures used in Example 1. The evaluation results thus obtained are listed in Table 1 given below.

Example 3

An aqueous phase was prepared by mixing 80.0 g of sasa albo-marginate, 30.0 g of D-sorbitol solution (Sorbit 70, water content: 30% by weight available from Towa Kasei Kogyo, Ltd.), 2.0 g of polyoxyethylene (40 moles) sorbit tetraoleate (LEODOL 440, HLB: 11.8 available from Kao Corporation) and 446.0 g of water and heating at 60° C. to give a solution. On the other hand, an oil phase was prepared by mixing 400.0 g of soybean oil, 40.0 g of decaglycerin decaoleate (SY GLYSTAR DAO-750, HLB: 3, available from Sakamoto Yakuhin Kogyo K.K.) and 2.0 g of citric acid monoglycelide (POEMU K-30, HLB: 3.0, available from Riken Vitamin Co., Ltd.) and then heating to 60° C. to give a solution. To the oil phase, there was slowly added the foregoing aqueous phase while they were mixed in a homomixer at 6000 rpm and 60° C. for 20 minutes to give an emulsion, followed by further emulsification in a high pressure homogenizer at a pressure of 100 kg/cm$^2$ and drying the emulsion using an oil pump to thus give a liquid brown oily composition containing sasa albo-marginate extract. The water content of the oily composition was found to be 0.3% by weight. The water content and the sasa albo-marginate extract content and the content of the sorbit pigment of the solid phase dispersed in the oil phase were found to be 1.6% by weight, 76.5% by weight and 20.1% by weight, respectively. The average particle size of the solid phase was determined to be 0.8 μm. The resulting oily composition was inspected for the storage stability according to the same procedures used in the foregoing Examples. The evaluation results thus obtained are listed in Table 1.

Comparative Example 1

There were mixed 50.0 g of a grape seed extract, 500.0 g of soybean oil and 50.0 g of POEMU PR-100 followed by heating the mixture to 60° C. to dissolve them. Then the mixture was further mixed and stirred in a homomixer at 6000 rpm and 60° C. for 20 minutes and pulverized in a sand grinder to give a liquid brown oily composition containing grape seed extract. The water content of the oily composition was found to be 0.2% by weight. The water content and the grape seed extract content of the solid phase dispersed in the oil phase were found to be 2.4% by weight 97.7% by weight, respectively. The average particle size of the solid phase was determined to be 8.6 μm. The resulting oily composition was inspected for the storage stability according to the same procedures used in Example 1. The evaluation results thus obtained are listed in Table 2.

Comparative Example 2

The same procedures used in Example 1 were repeated to give a brown W/O type emulsion containing grape seed extract. The water content in the emulsion was found to be 40.0% by weight. The water content and the grape seed extract content of the solid phase dispersed in the oil phase were found to be 88.9% by weight 11.1% by weight, respectively. The average particle size of the solid phase was determined to be 1.1 μm. The resulting oily composition was inspected for the storage stability according to the same procedures used in Example 1. The evaluation results thus obtained are listed in Table 2.

Comparative Example 3

The same procedures used in Example 1 were repeated to give a W/O type emulsion. Then the W/O type emulsion was dried using an oil pump for a time shorter than that used in Example 1 to give a liquid brown oily composition containing the grape seed extract, whose water content was higher than that observed in Example 1. The water content in the emulsion was found to be 4.1% by weight. The water content and the grape seed extract content of the solid phase dispersed in the oil phase were found to be 33.9% by weight and 66.1% by weight, respectively. The average particle size of the solid phase was determined to be 0.8 μm. The resulting oily composition was inspected for the storage stability according to the same procedures used in Example 1. The evaluation results thus obtained are listed in Table 2.

Comparative Example 4

The same procedures used in Example 2 were repeated to give a W/O type emulsion. Then the W/O type emulsion was dried using an oil pump for a time shorter than that used in Example 2 to give a liquid dark blue oily composition containing the blueberry extract, whose water content was higher than that observed in Example 2. The water content in the emulsion was found to be 9.5% by weight. The water content, the blueberry extract content and the glycerin content of the solid phase dispersed in the oil phase were found to be 32.8% by weight, 48.0% by weight and 19.2% by weight, respectively. The average particle size of the solid phase was determined to be 1.1 μm. The resulting oily composition was inspected for the storage stability according to the same procedures used in Example 1. The evaluation results thus obtained are listed in Table 2.

Comparative Example 5

The same procedures used in Example 3 were repeated to give a W/O type emulsion. Then the W/O type emulsion was dried using an oil pump for a time shorter than that used in Example 3 to give a liquid brown oily composition containing the sasa albo-marginate extract, whose water content was higher than that observed in Example 3. The water content in the emulsion was found to be 8.8% by weight. The water content, the sasa albo-marginate extract content and the sorbit content of the solid phase dispersed in the oil phase were found to be 33.8% by weight, 51.4% by weight and 13.5% by weight, respectively. The average particle size of the solid phase was determined to be 0.9 μm. The resulting oily composition was inspected for the storage stability according to the same procedures used in Example 1. The evaluation results thus obtained are listed in Table 2.

Comparative Example 6

An aqueous phase was prepared by mixing 100.0 g of blueberry extract, 40.0 g of glycerin and 350.0 g of a 25% by weight aqueous ethanol solution and then heated to 60° C. Separately, an oil phase was prepared by mixing 450.0 g of soybean oil, 30.0 g of Tocopherol 100 and 30.0 g of POEMU PR-100 and then heating the mixture to 60° C. The oil phase was slowly added to the oil phase and then stirred with spatula for 20 minutes to emulsify the mixture. After the emulsification, the emulsion was dehydrated under reduced pressure using an oil pump to give a liquid dark blue oily composition containing the blueberry extract. The content of the aqueous ethanol solution in the oily composition was found to be 0.2% by weight. The aqueous ethanol solution content, the blueberry extract content and the glycerin content of the solid phase dispersed in the oil phase were found to be 0.9% by weight, 70.8% by weight and 28.3% by weight, respectively. The average particle size of the solid phase was determined to be 6.8 μm. The resulting oily composition was inspected for the storage stability according to the same procedures used in Example 1. The evaluation results thus obtained are listed in Table 2.

TABLE 1

Results of Storage Stability Evaluation

| Ex. No. | | 1 | 2 | 3 |
|---|---|---|---|---|
| Immediately after Preparation | | ◉ | ◉ | ◉ |
| 5° C. | one month | ◉ | ◉ | ◉ |
| | three months | ○ | ○ | ○ |
| | six months | ○ | ○ | ○ |
| Room temp. | one month | ◉ | ◉ | ◉ |
| | three months | ○ | ○ | ○ |
| | six months | Δ | Δ | Δ |
| 40° C. | one month | ○ | ○ | ○ |
| | three months | Δ | Δ | Δ |
| | six months | Δ□ | Δ□ | Δ□ |

TABLE 2

Results of Storage Stability Evaluation

| Comp. Ex. No. | 1 | 2 | 3 | 4 | 5 | 6 |
|---|---|---|---|---|---|---|
| Immediately after Preparation | ○ | ◉ | ◉ | ◉ | ◉ | ◉ |
| 5° C. | | | | | | |
| one month | ○□ | ○□ | ○ | ○ | ○ | Δ□ |
| three months | ▲■ | ○□X | ○□ | ○□ | ○□ | ▲■ |
| six Months | ▲■ | ▲■X | ▲■ | ▲■ | ▲■ | ▲■ |
| Room Temp. | | | | | | |
| one month | ○■ | ○□X | ○□ | ○□ | ○□ | Δ■ |
| three months | ▲■ | ▲■X | Δ□ | Δ□ | Δ□ | ▲■ |
| six Months | ▲■ | ▲■X | ▲■X | ▲■X | ▲■X | ▲■ |
| 40° C. | | | | | | |
| one month | ▲■ | ▲■X | ▲■ | ▲■ | ▲■ | ▲■ |
| three months | ▲■ | ▲■X | ▲■X | ▲■X | ▲■X | ▲■ |
| six Months | ▲■ | ▲■X | ▲■X | ▲■X | ▲■X | ▲■ |

[Confirmation of Taste-Masking Effect]

Various kinds of the oily compositions and emulsified compositions containing aqueous effective substances and prepared in Examples 1 to 3 and Comparative Examples 1 to 6 were inspected for the taste-masking effect thereof by getting 20 normal persons to eat them and to judge whether they could be conscious of the taste of the aqueous effective substances or not. The results thus obtained are summarized in the following Table 3.

TABLE 3

Results of Sensory Test (Number of Persons)

| Ex. No. | 1 | 2 | 3 | 1* | 2* | 3* | 4* | 5* | 6* |
|---|---|---|---|---|---|---|---|---|---|
| ○ | 2 | 1 | 0 | 0 | 0 | 0 | 0 | 0 | 0 |
| Δ | 18 | 19 | 20 | 0 | 0 | 0 | 0 | 0 | 0 |
| X | 0 | 0 | 0 | 20 | 20 | 20 | 20 | 20 | 20 |

○: The panelists were not conscious of the taste of the aqueous effective substance.
Δ: The panelists were slightly conscious of the taste of the aqueous effective substance.
X: The panelists were conscious of the taste of the aqueous effective substance.
*Comparative Example Example 4

An aqueous phase was prepared by mixing 60.0 g of Fomes japonicus powder, 27.0 g of gelatin (Gelatin A-U available from Miyagi Chemical Industries, Ltd.) and 413.0 g of water and then heating the mixture to 60° C. On the other hand, an oil phase was separately prepared by mixing 400.0 g of soybean oil, 50.0 g of a refined fish oil (DHA-27 available from Tama Biochemical Co., Ltd.) and 50.0 g of tetraglycerin pentaoleate (SY GLYSTAR PO-310, HLB: 2, available from Sakamoto Yakuhin Kogyo K.K.) and then heating the mixture to 60° C. To the oil phase, there was slowly added the foregoing aqueous phase while they were mixed in a homomixer at 6000 rpm and 60° C. for 20 minutes to give an emulsion, followed by diying the emulsion using an oil pump to thus give a liquid brown oily composition containing Fomes japonicus extract. The water content of the oily composition was found to be 0.5% by weight. The water content and the Fomes japonicus extract content of the solid phase dispersed in the oil phase were found to be 3.3% by weight and 66.7% by weight, respectively. Moreover, the amount of the gelatin present in the solid phase was found to be 45.0% by weight per 100 parts by weight of the Fomes japonicus extract. The average particle size of the solid phase was determined to be 0.5 μm. The resulting oily composition was inspected for the storage stability according to the same procedures used in Example 1. The evaluation results thus obtained are listed in Table 4.

The resulting oily composition (1 g) was mixed with 99 g of soybean oil to give white diluted oil of the oily composition.

Example 5

An aqueous phase was prepared by mixing 100.0 g of tea extract (Sunphenone, available from Taiyo Chemical Co., Ltd.), 8.0 g of Gelatin A-U and 497.0 g of a 20% by weight aqueous ethanol solution and then heating the resulting mixture to 60° C. Separately, an oil phase was prepared by mixing 350.0 g of soybean oil, 5.0 g of hardened soybean oil (Hardened Soybean Oil 34° available from The Nissin Oil Mills, Ltd.), 30.0 g of polyglycerin condensed ricinoleate (POEMU PR-300, HLB: 1.7 available from Riken Vitamin Co., Ltd.) and 10.0 g of a glycerin fatty acid monoester (EMULGY MU, HLB: 4.2, available from Riken Vitamin Co., Ltd.) and then heating the resulting mixture to 60° C.

Subsequently, the same procedures used in Example 4 were repeated to give a liquid brown oily composition containing the tea extract. The aqueous ethanol solution content of the oily composition was found to be 0.1% by weight. The aqueous ethanol solution content and the tea extract content of the solid phase dispersed in the oil phase were found to be 0.5% by weight and 92.2% by weight, respectively. Moreover, the amount of the gelatin relative to 100 parts by weight of the tea extract was found to be 8.0 parts by weight. In addition, the gelatin content in the solid phase was found to be 7.4% by weight. The average particle size of the solid phase was determined to be 0.7 μm. The resulting oily composition was inspected for the storage stability according to the same procedures used in Example 1. The evaluation results thus obtained are listed in Table 4.

Example 6

An aqueous phase (60° C.) was prepared by mixing and dissolving 80.0 g of a rosemary extract (RM21C, available from Tokyo Tanabe Seiyaku Co., Ltd.), 10.0 g of gum arabic (ARABIC COLE SS available from Sanei Yakuhin Boeki K.K.), 2.0 g of tetraoleic acid polyoxyethylene (40 moles) sorbit (LEODOL 440, HLB: 11.8, available from Kao Corporation) and 558.0 g of water. Separately, an oil phase was prepared by mixing 200.0 g of glyceryl tri-2-ethylhexanoate (TIO, available from The Nissin Oil Mills, Ltd.), 100.0 g of liquid paraffin, 5.0 g of bees wax, 40.0g of POEMU PR-300 and 5.0 g of hydrogenated lecithin (BASIS LP-20H, available from The Nissin Oil Mills, Ltd.) and then heating the mixture to 60° C. To the oil phase, there was slowly added the foregoing aqueous phase while they were mixed in a homomixer at 6000 rpm and 60° C. for 20 minutes to give an emulsion, followed by further emulsification in a high pressure homogenizer at a pressure of 100 kg/cm$^2$ and drying the emulsion using an oil pump to thus give a liquid yellowish white oily composition containing rosemary extract. The water content of the oily composition was found to be 0.3% by weight. The water content and the rosemary extract content of the solid phase dispersed in the oil phase were found to be 1.4% by weight and 85.7% by weight, respectively. Moreover, the amount of the gum arabic relative to 100 parts by weight of the rosemary extract was found to be 12.5 parts by weight. In addition, the gum arabic content in the solid phase was found to be 10.7% by weight. The average particle size of the solid phase was determined to be 0.3 μm. The resulting oily composition was inspected for the storage stability according to the same procedures used in Example 1. The evaluation results thus obtained are listed in Table 4.

Example 7

Propolis (100.0 g), Gelatin A-U (30.0 g), a sacchaiified liquid product of reduced starch (50.0 g; AMAMEAL, water content: 30% by weight, available from Towa Kasei Kogyo K.K.), guar gum (1.0 g, BISTOP B-20, available from Saneigen F.F.I. K.K.) and water (419.0 g) were mixed and dissolved to give an aqueous phase (60° C.). On the other hand, 350.0 g of soybean oil and 50.0 g of hexaglycerin monooleate (SY GLYSTAR PO-500, HLB: 4, available from Sakamoto Yakuhin Kogyo K.K.) were mixed together and then heated to 60° C. to give an oil phase. Subsequently, the same procedures used in Example 4 were repeated to give a liquid yellowish white oily composition containing the propolis. The water content of the oily composition was found to be 3.8% by weight. The water content and the propolis content of the solid phase dispersed in the oil phase were found to be 11.9% by weight and 53.1% by weight, respectively. Moreover, the amount of the gelatin relative to 100 parts by weight of the propolis was found to be 30 parts by weight. In addition, the gelatin content and the content of the saccharified product of reduced starch in the solid phase were found to be 15.9% by weight and 18.6% by weight, respectively. The average particle size of the solid phase was determined to be 1.0 μm. The resulting oily composition was inspected for the storage stability according to the same procedures used in Example 1. The evaluation results thus obtained are listed in Table 4.

Example 8

There were mixed 100.0 g of ginseng extract, 20.0 g of Gelatin A-U, 20.0 g of ARABIC COLE SS, 70.0 g of glycerin, 2.0 g of enzyme-decomposed lecithin (BASIS LG-10K, available from The Nissin Oil Mills, Ltd.) and 358.0 g of water to give an aqueous phase (60° C.). Separately, an oil phase was prepared by mixing 350.0 g of a middle chain fatty acid triglyceride (ODO, available from The Nissin Oil Mills, Ltd.), 30.0 g of dl-α-tocopherol, 40.0 g of POEMU PR-300 and 10.0 g of citric acid monoglyceride (POEMU K-30, HLB: 3, available from Riken Vitamin Co., Ltd.), followed by heating the mixture to 60° C. Subsequently, the same procedures used in Example 4 were repeated to give a liquid brown oily composition containing the ginseng extract. The water content of the oily composition was found to be 0% by weight. The water content and the ginseng extract content of the solid phase dispersed in the oil phase were found to be 0% by weight and 47.2% by weight, respectively. Moreover, the amount of the gelatin and gum arabic relative to 100 parts by weight of the ginseng extract was found to be 40 parts by weight. In addition, the content of gelatin and gum arabic and the glycerin content in the solid phase were found to be 18.9% by weight and 33.0% by weight, respectively. The average particle size of the solid phase was determined to be 0.4 μm. The resulting oily composition was inspected for the storage stability according to the same procedures used in Example 1. The evaluation results thus obtained are listed in Table 4.

Comparative Example 7

The same procedures used in Example 4 were repeated to give a brown Fomes japonicus-containing W/O type emulsion. The water content of the emulsion was found to be 41.3% by weight. The water content and the Fomes japonicus extract content of the solid phase dispersed in the oil phase were found to be 82.6% by weight and 12.0% by weight, respectively. Moreover, the amount of the gelatin relative to 100 parts by weight of the Fomes japonicus extract was found to be 45.0 parts by weight. In addition, the content of gelatin in the solid phase was found to be 5.4% by weight. The average particle size of the solid phase was determined to be 0.9 μm. The resulting emulsion was inspected for the storage stability according to the same procedures used in Example 1. The evaluation results thus obtained are listed in Table 5.

Comparative Example 8

The same procedures used in Example 4 were repeated to give a W/O type emulsion. Then the W/O type emulsion was dried using an oil pump for a time shorter than that used in Example 4 to give a liquid brown Fomes japonicus extract-containing oily composition, whose water content was higher than that observed in Example 4. The water content of the oily composition was found to be 7.1% by weight. The water content and the Fomes japonicus extract content of the solid phase dispersed in the oil phase were found to be 34.0% by weight and 45.5% by weight, respectively. Moreover, the amount of the gelatin relative to 100 parts by weight of the Fomes japonicus extract was found to be 45.0 parts by weight. In addition, the content of gelatin in the solid phase was found to be 20.5% by weight. The average particle size of the solid phase was determined to be 0.7 μm. The resulting oily composition was inspected for the storage stability according to the same procedures used in Example 1. The evaluation results thus obtained are listed in Table 5.

Comparative Example 9

The same procedures used in Example 5 were repeated to give a W/O type emulsion. Then the W/O type emulsion was dried using an oil pump for a time shorter than that used in Example 5 to give a liquid brown tea extract-containing oily composition, whose water content was higher than that observed in Example 5. The water content of the oily composition was found to be 10.3% by weight. The water content and the tea extract content of the solid phase dispersed in the oil phase were found to be 34.8% by weight and 60.3% by weight, respectively. Moreover, the amount of the gelatin relative to 100 parts by weight of the tea extract was found to be 8.0 parts by weight. In addition, the content of gelatin in the solid phase was found to be 4.8% by weight. The average particle size of the solid phase was determined to be 0.9 μm. The resulting oily composition was inspected for the storage stability according to the same procedures used in Example 1. The evaluation results thus obtained are listed in Table 5.

Comparative Example 10

The same procedures used in Example 6 were repeated to give a W/O type emulsion. Then the W/O type emulsion was dried using an oil pump for a time shorter than that used in Example 6 to give a liquid yellowish white rosemary extract-containing oily composition, whose water content was higher than that observed in Example 6. The water content of the oily composition was found to be 9.7% by weight. The water content and the rosemary extract content of the solid phase dispersed in the oil phase were found to be 34.0% by weight and 57.4% by weight, respectively. Moreover, the amount of the gum arabic relative to 100 parts by weight of the rosemary extract was found to be 12.5 parts by weight. In addition, the content of gum arabic in the solid phase was found to be 7.2% by weight. The average particle size of the solid phase was determined to be 0.6 μm. The resulting oily composition was inspected for the storage stability according to the same procedures used in Example 1. The evaluation results thus obtained are listed in Table 5.

Comparative Example 11

The same procedures used in Example 7 were repeated to give a W/O type emulsion. Then the W/O type emulsion was dried using an oil pump for a time shorter than that used in Example 7 to give a liquid yellowish white propolis-containing oily composition, whose water content was higher than that observed in Example 7. The water content of the oily composition was found to be 12.7% by weight. The water content and the propolis content of the solid phase dispersed in the oil phase were found to be 33.2% by weight and 40.3% by weight, respectively. Moreover, the amount of the gelatin relative to 100 parts by weight of the propolis was found to be 30 parts by weight. In addition, the content of gelatin and the content of the saccharified product of reduced starch in the solid phase were found to be 12.1% by weight and 14.1% by weight, respectively. The average particle size of the solid phase was determined to be 1.2 μm. The resulting oily composition was inspected for the storage stability according to the same procedures used in Example 1. The evaluation results thus obtained are listed in Table 6.

Comparative Example 12

The same procedures used in Example 8 were repeated to give a W/O type emulsion. Then the W/O type emulsion was dried using an oil pump for a time shorter than that used in Example 8 to give a liquid brown ginseng extract-containing oily composition, whose water content was higher than that observed in Example 8. The water content of the oily composition was found to be 14.7% by weight. The water content and the ginseng extract content of the solid phase dispersed in the oil phase were found to be 34.3% by weight and 31.0% by weight, respectively. Moreover, the amount of the gelatin and gum arabic relative to 100 parts by weight of the ginseng extract was found to be 40 parts by weight. In addition, the content of gelatin and gum arabic and the content of the glycerin in the solid phase were found to be 12.4% by weight and 21.7% by weight, respectively. The average particle size of the solid phase was determined to be 0.7 μm. The resulting oily composition was inspected for the storage stability according to the same procedures used in Example 1. The evaluation results thus obtained are listed in Table 6.

Comparative Example 13

An aqueous phase was prepared by mixing 100.0 g of SUNPHENONE, 8.0 g of Gelatin A-U and 497.0 g of a 20% by weight aqueous ethanol solution and then heating the mixture to 60° C. Separately, an oil phase was prepared by mixing 350.0 g of soybean oil, 5.0 g of hardened soybean oil 34°, 30.0 g of POEMU PR-300 and 10.0 g of EMULGY MU and dissolving them with heating at 60° C. To the oil phase, there was slowly added the oil phase, followed by emulsification by stirring with a spatula for 20 minutes. After the emulsification, the emulsion was dehydrated under reduced pressure using an oil pump to give a liquid brown tea extract-containing oily composition. The aqueous ethanol solution content of the oily composition was found to be 0.3% by weight. The aqueous ethanol solution content and the tea extract content of the solid phase dispersed in the oil phase were found to be 1.4% by weight and 91.3% by weight, respectively. Moreover, the amount of the gelatin relative to 100 parts by weight of the tea extract was found to be 8.0 parts by weight. In addition, the content of gelatin in the solid phase was found to be 7.3% by weight. The average particle size of the solid phase was determined to be 7.0 μm. The resulting oily composition was inspected for the storage stability according to the same procedures used in Example 1. The evaluation results thus obtained are listed in Table 6.

TABLE 4

Results of Storage Stability Evaluation

| Ex. No. | | 4 | 5 | 6 | 7 | 8 |
|---|---|---|---|---|---|---|
| Immediately After Preparation | | ⊚ | ⊚ | ⊚ | ⊚ | ⊚ |
| 5° C. | one month | ⊚ | ⊚ | ⊚ | ⊚ | ⊚ |
| | three months | ⊚ | ⊚ | ⊚ | ⊚ | ⊚ |
| | six months | ⊚ | ⊚ | ⊚ | ⊚ | ⊚ |
| Room Temp. | one month | ⊚ | ⊚ | ⊚ | ⊚ | ⊚ |
| | three months | ⊚ | ⊚ | ⊚ | ⊚ | ⊚ |
| | six months | ⊚ | ○ | ○ | ⊚ | ⊚ |

TABLE 4-continued

Results of Storage Stability Evaluation

| Ex. No. | | 4 | 5 | 6 | 7 | 8 |
|---|---|---|---|---|---|---|
| 40° C. | one month | ⊚ | ⊚ | ⊚ | ⊚ | ⊚ |
| | three months | ⊚ | ○ | ○ | ⊚ | ⊚ |
| | six months | ⊚ | ○ | ○ | ⊚ | ⊚ |

TABLE 5

Results of Storage Stability Evaluation

| Comparative Example No. | | 7 | 8 | 9 | 10 |
|---|---|---|---|---|---|
| Immediately After Preparation | | ⊚ | ⊚ | ⊚ | ⊚ |
| 5° C. | one month | ○□ | ○ | ○ | ○ |
| | three months | ○□X | ○□ | ○□ | ○□ |
| | six months | ▲■X | Δ□ | Δ□ | Δ□ |
| Room Temp. | one month | ○□X | ○□ | ○□ | ○□ |
| | three months | ▲■X | Δ□ | Δ□ | Δ□ |
| | six months | ▲■X | Δ■X | ▲■X | ▲■X |
| 40° C. | one month | ▲■X | Δ□ | Δ□ | Δ□ |
| | three months | ▲■X | Δ■X | ▲■X | ▲■X |
| | six months | ▲■X | ▲■X | ▲■X | ▲■X |

TABLE 6

Results of Storage Stability Evaluation

| Comparative Example No. | | 11 | 12 | 13 |
|---|---|---|---|---|
| Immediately After Preparation | | ⊚ | ⊚ | ○ |
| 5° C. | one month | ○ | ○ | Δ□ |
| | three months | ○□ | ○□ | Δ■ |
| | six months | Δ□ | Δ□ | ▲■ |
| Room Temp. | one month | ○□ | ○□ | Δ■ |
| | three months | Δ□ | Δ□ | ▲■ |
| | six months | ▲■X | Δ■X | ▲■ |
| Room Temp. | one month | Δ□ | Δ□ | ▲■ |
| | three months | Δ■X | Δ■X | ▲■ |
| | six months | ▲■X | ▲■X | ▲■ |

[Confirmation of Taste-Masking Effect]

Various kinds of the oily compositions and emulsified compositions containing aqueous effective substances and prepared in Examples 4, 5, 7 and 8 and Comparative Examples 7 to 13 were inspected for the taste-masking effect thereof by getting 20 normal persons to eat them and to judge whether they could be conscious of the taste of the aqueous effective substances or not. The results thus obtained are summarized in the following Table 7.

TABLE 7

Results of Sensory Test (number of persons)

| Ex. No. | 4 | 5 | 7 | 8 | 7* | 8* | 9* | 10* | 11* | 12* | 13* |
|---|---|---|---|---|---|---|---|---|---|---|---|
| ○ | 20 | 18 | 20 | 20 | 0 | 0 | 0 | 0 | 0 | 0 | 0 |
| Δ | 0 | 2 | 0 | 0 | 0 | 0 | 0 | 0 | 0 | 0 | 0 |
| X | 0 | 0 | 0 | 0 | 20 | 20 | 20 | 20 | 20 | 20 | 20 |

*Comparative Example
○: The panelists were not conscious of the taste of the aqueous effective substance.
Δ: The panelists were slightly conscious of the taste of the aqueous effective substance.
X: The panelists were conscious of the taste of the aqueous effective substance.

Example 9

An aqueous phase was prepared by mixing 80.0 g of Fomes japonicus powder, 110.0 g of pullulan (Pullulan, available from Ringen Co., Ltd.), 1.0 g of tetraoleic acid polyoxyethylene (40 moles) sorbit (LEODOL 440, HLB: 11.8, available from Kao Corporation) and 424.0 g of water and then heating the mixture to 60° C. Separately, an oil phase was prepared by mixing 350.0 g g of soybean oil, 5.0 g of hardened soybean oil (Hardened Soybean Oil 34° available from The Nissin Oil Mills, Ltd.) and 30.0 g of polyglycerin condensed ricinoleate (POEMU PR-300, HLB: 1.7, available from Riken Vitamin Co., Ltd.) and then dissolving them with heating to 60° C. To the oil phase, there was slowly added to the aqueous phase while mixing and emulsifying them at 6000 rpm and 60° C. for 20 minutes using a homomixer and then the mixture was dried using an oil pump to give a liquid brown oily composition containing Fomes japonicus extract. The water content of the oily composition was found to be 0% by weight. The water content and the Fomes japonicus extract content of the solid phase dispersed in the oil phase were found to be 0% by weight and 41.9% by weight, respectively. Moreover, the amount of the pullulan relative to 100 parts by weight of the Fomes japonicus extract was found to be 137.5 parts by weight. In addition, the content of pullulan in the solid phase was found to be 57.6% by weight. The average particle size of the solid phase was determined to be 0.4 $\mu$m. The resulting oily composition was inspected for the storage stability according to the same procedures used in Example 1. The evaluation results thus obtained are listed in Table 8.

The resulting oily composition (1 g) was mixed with 99 g of soybean oil to give white diluted oil of the oily composition.

Example 10

An aqueous phase was prepared by mixing 80.0 g of tea extract (Sunphenone, available from Taiyo Chemical Co., Ltd.), 20.0 g of water-soluble corn fibers (CELL ACE#40, available from Nihon Shokuhin Kako Co., Ltd.), 20.0 g of liquid D-sorbitol (Sorbit L-70, water content: 30% by weight, available from Towa Kasei Kogyo K.K.) and 450.0 g of a 20% by weight aqueous ethanol solution, and then heating the mixture to 60° C. Separately, an oil phase was prepared by mixing 400.0 g of soybean oil, 28.0 g of tetraglycerin condensed ricinoleate (SY GLYSTAR CR-310, HLB: 2, available from Sakamoto Yakuhin Kogyo K.K.) and 2.0 g of glycenin fatty acid monoester (EMULGY MU, HLB: 4.2 available from Riken Vitamin Co., Ltd.) and then dissolving them with heating to 60° C. Subsequently, the same procedures used in Example 9 were repeated to give a liquid brown tea extract-containing oily composition. The aqueous ethanol solution content of the oily composition was found to be 0.5% by weight. The aqueous ethanol solution content and the tea extract content of the solid phase dispersed in the oil phase were found to be 2.3% by weight and 68.5% by weight, respectively. Moreover, the amount of the corn fibers relative to 100 parts by weight of the tea extract was found to be 25.0 parts by weight. In addition, the content of corn fibers and the sorbit content in the solid phase were found to be 17.1% by weight and 12.0% by weight, respectively. The average particle size of the solid phase was determined to be 0.5 $\mu$m. The resulting oily composition was inspected for the storage stability according to the same procedures used in Example 1. The evaluation results thus obtained are listed in Table 8.

Example 11

An aqueous phase (60° C.) was prepared by mixing 100.0 g of rosemary extract (RM21C, available from Tokyo Tanabe Seiyaku Co., Ltd.), 65.0 g of water-soluble corn fibers (CELL ACE#25 available from Nihon Shokuhin Kako Co., Ltd.), 1.0 g of guar gum (BISTOP B-20, available from Saneigen F.F.I. K.K.) and 432.0 g of water. On the other hand, an oil phase was prepared by mixing 300.0 g of soybean oil, 50.0 g of mixed tocopherol (Tocopherol 100, available from The Nissin Oil Mills, Ltd.), 50.0 g of hexaglycerin pentaoleate (SY GLYSTAR PO-500, HLB: 4, available from Sakamoto Yakuhin Kogyo K.K.) and 2.0 g of citric acid monoglycelide (POEMU K-30, HLB: 3, available from Riken Vitamin Co., Ltd.) and then dissolving them with heating at 60° C. To this oil phase, there was slowly added the aqueous phase, while mixing and emulsifying the mixture at 6000 rpm and 60° C. for 20 minutes, using a homomixer, followed by further emulsifying at a pressure of 100 kg/cm$^2$ using a high pressure homogenizer and then drying the resulting emulsion using an oil pump to give a liquid yellow rosemary extract-containing oily composition. The water content of the oily composition was found to be 0.8% by weight. The water content and the rosemary extract content of the solid phase dispersed in the oil phase were found to be 2.7% by weight and 58.6% by weight, respectively. Moreover, the amount of the corn fibers relative to 100 parts by weight of the rosemary extract was found to be 65 parts by weight. In addition, the content of corn fibers in the solid phase was found to be 38.1% by weight. The average particle size of the solid phase was determined to be 0.3 $\mu$m. The resulting oily composition was inspected for the storage stability according to the same procedures used in Example 1. The evaluation results thus obtained are listed in Table 8.

Example 12

An aqueous phase (60° C.) was prepared by mixing 60.0 g of ascorbic acid, 80.0 g of water-soluble soybean fibers (Soyafibe-S available from Fuji Oil Co., Ltd.), 40.0 g of a saccharified liquid product of reduced starch (AMAMEAL, water content: 30% by weight, available from Towa Kasei Kogyo K.K.) and 420.0 g of water. Separately, an oil phase was prepared by mixing 300.0 g of soybean oil, 50.0 g of refined fish oil (DHA-27 available from Tama Biochemical Co., Ltd.) and 50.0 g of tetraglycerin tiistearate (SY GLYSTAR TS-310, HLB: 4, available from Sakamoto Yakuhin Kogyo K.K.) and then dissolving them with heating at 60° C. Subsequently, the same procedures used in Example 9 were repeated to give a liquid white ascorbic acid-containing oily composition. The water content of the oily composition was found to be 0.2% by weight. The water content and the ascorbic acid content of the solid phase dispersed in the oil phase were found to be 0.7% by weight and 35.5% by weight, respectively. Moreover, the amount of the soybean fibers relative to 100 parts by weight of the ascorbic acid was found to be 133.3 parts by weight. In addition, the content of soybean fibers and the content of the saccharified liquid product of reduced starch in the solid phase were found to be 47.3% by weight and 16.6% by weight, respectively. The average particle size of the solid phase was determined to be 0.5cm. The resulting oily composition was inspected for the storage stability according to the same procedures used in Example 1. The evaluation results thus obtained are listed in Table 8.

Example 13

An aqueous phase (60° C.) was prepared by mixing and dissolving 50.0 g of vitamin B1, 50.0 g of polyvinyl alcohol, 20.0 g of glycerin, 2.0 g of enzyme-decomposed lecithin (BASIS LG-10K available from The Nissin Oil Mills, Ltd.) and 486.0 g of water. On the other hand, an oil phase was prepared by mixing 250.0 g of glyceryl tri-2-ethylhexanoate (ITO available from The Nissin Oil Mills, Ltd.), 100.0 g of liquid paraffin, 2.0 g of bees wax, 30.0 g of POEMU PR-300 and 10.0 g of hydrogenated lecithin (BASIS LP-20H, available from The Nissin Oil Mills, Ltd.) and then dissolving them with heating at 50° C. Subsequently, the same procedures used in Example 9 were repeated to give a liquid yellow vitamin B1-containing oily composition. The water content of the oily composition was found to be 1.3% by weight. The water content and the vitamin B1 content of the solid phase dispersed in the oil phase were found to be 5.3% by weight and 38.8% by weight, respectively. Moreover, the amount of the polyvinyl alcohol relative to 100 parts-by weight of the vitamin B1 was found to be 100 parts by weight. In addition, the content of the polyvinyl alcohol and the glycerin content in the solid phase were found to be 38.8% by weight and 15.5% by weight, respectively. The average particle size of the solid phase was determined to be 1.0 $\mu$m. The resulting oily composition was inspected for the storage stability according to the same procedures used in Example 1. The evaluation results thus obtained are listed in Table 6.

Example 14

An aqueous phase was prepared by mixing 20.0 g of codeine phosphate, 40.0 g of pullulan (Pullulan, available from Ringen Co., Ltd.), 10.0 g of glycerin and 480.0 g of water and then heating the mixture to 45° C. Separately, an oil phase was prepared by mixing 400.0 g of a middle chain fatty acid triglyceride (ODO, available from The Nissin Oil Mills, Ltd.), 10.0 g of dl-α-tocopherol and 40.0 g of POEMU PR-300 and then dissolving them with heating at 60° C. To the oil phase, there was slowly added the aqueous phase while mixing and emulsifying them at 6000 rpm and 45° C. for 20 minutes using a homomixer, followed by drying the resulting emulsion using an oil pump to give a liquid white codeine phosphate-containing oily composition. The water content of the oily composition was found to be 0.4% by weight. The water content and the codeine phosphate content of the solid phase dispersed in the oil phase were found to be 2.9% by weight and 27.7% by weight, respectively. Moreover, the amount of the pullulan relative to 100 parts by weight of the codeine phosphate was found to be 200 parts by weight. In addition, the content of the pullulan and the glycerin content in the solid phase were found to be 55.5% by weight and 13.9% by weight, respectively. The average particle size of the solid phase was determined to be 0.5 $\mu$m. The resulting oily composition was inspected for the storage stability according to the same procedures used in Example 1. The evaluation results thus obtained are listed in Table 6.

Comparative Example 14

The same procedures used in Example 9 were repeated to give a brown Fomes japonicus extract-containing W/O type emulsion. The water content of the emulsion was found to be 42.4% by weight. The water content and the Fomes japonicus extract content of the aqueous phase dispersed in the oil phase were found to be 68.9% by weight and 13.0% by weight, respectively. Moreover, the amount of the pullulan relative to 100 parts by weight of the Fomes japonicus extract was found to be 137.5 parts by weight. In addition, the content of the pullulan in the aqueous phase was found to be 17.9% by weight. The average particle size of the aqueous phase was determined to be 0.9 $\mu$m. The resulting emulsion was inspected for the storage stability according to the same procedures used in Example 1. The evaluation results thus obtained are listed in Table 9.

Comparative Example 15

The same procedures used in Example 9 were repeated to give a W/O type emulsion. Then the W/O type emulsion was dried using an oil pump for a time shorter than that used in Example 9 to give a liquid brown Fomes japonicus extract-containing oily composition, whose water content was greater than that observed in Example 9. The water content of the oily composition was found to be 14.1% by weight. The water content and the Fomes japonicus extract content of the aqueous phase dispersed in the oil phase were found to be 33.1% by weight and 28.0% by weight, respectively. Moreover, the amount of the pullulan relative to 100 parts by weight of the Fomes japonicus extract was found to be 137.5 parts by weight. In addition, the content of the pullulan in the aqueous phase was found to be 38.5% by weight. The average particle size of the aqueous phase was determined to be 0.6 $\mu$m. The resulting oily composition was inspected for the storage stability according to the same procedures used in Example 1. The evaluation results thus obtained are listed in Table 9.

Comparative Example 16

The same procedures used in Example 10 were repeated to give a W/O type emulsion. Then the W/O type emulsion was dried using an oil pump for a time shorter than that used in Example 10 to give a liquid brown tea extract-containing oily composition, whose water content was greater than that observed in Example 10. The water content of the oily composition was found to be 10.3% by weight. The water content and the tea extract content of the aqueous phase dispersed in the oil phase were found to be 35.4% by weight and 45.3% by weight, respectively. Moreover, the amount of the corn fibers relative to 100 parts by weight of the tea extract was found to be 25 parts by weight. In addition, content of the corn fibers and the sorbit content in the aqueous phase were found to be 11.3% by weight and 7.9% by weight, respectively. The average particle size of the aqueous phase was determined to be 0.8 $\mu$m. The resulting oily composition was inspected for the storage stability according to the same procedures used in Example 1. The evaluation results thus obtained are listed in Table 9.

Comparative Example 17

The same procedures used in Example 11 were repeated to give a W/O type emulsion. Then the W/O type emulsion was dried using an oil pump for a time shorter than that used in Example 11 to give a liquid yellow rosemary extract-containing oily composition, whose water content was greater than that observed in Example 11. The water content of the oily composition was found to be 13.3% by weight. The water content and the rosemary extract content of the aqueous phase dispersed in the oil phase were found to be 34.4% by weight and 39.5% by weight, respectively. Moreover, the amount of the corn fibers relative to 100 parts by weight of the rosemary extract was found to be 65.0 parts by weight. In addition, the content of the corn fibers in the aqueous phase was found to be 25.7% by weight. The average particle size of the aqueous phase was determined to be 0.6 $\mu$m. The resulting oily composition was inspected for the storage stability according to the same procedures used in Example 1. The evaluation results thus obtained are listed in Table 9.

Comparative Example 18

The same procedures used in Example 12 were repeated to give a W/O type emulsion. Then the W/O type emulsion was dried using an oil pump for a time shorter than that used in Example 12 to give a liquid white ascorbic acid-containing oily composition, whose water content was greater than that observed in Example 12. The water content of the oily composition was found to be 12.7% by weight. The water content and the ascorbic acid content of the aqueous phase dispersed in the oil phase were found to be 33.0% by weight and 23.9% by weight, respectively. Moreover, the amount of the soybean fibers relative to 100 parts by weight of the ascorbic acid was found to be 133.3 parts by weight. In addition, the content of the soybean fibers and the content of the saccharified product of reduced starch in the aqueous phase were found to be 31.9% by weight and 11.2% by weight, respectively. The average particle size of the aqueous phase was determined to be 0.8 µm. The resulting oily composition was inspected for the storage stability according to the same procedures used in Example 1. The evaluation results thus obtained are listed in Table 10.

Comparative Example 19

The same procedures used in Example 13 were repeated to give a W/O type emulsion. Then the W/O type emulsion was dried using an oil pump for a time shorter than that used in Example 13 to give a liquid yellow vitamin B1-containing oily composition, whose water content was greater than that observed in Example 13. The water content of the oily composition was found to be 10.8% by weight. The water content and the vitamin B1 content of the aqueous phase dispersed in the oil phase were found to be 33.8% by weight and 27.1% by weight, respectively. Moreover, the amount of the polyvinyl alcohol relative to 100 parts by weight of the vitamin B1 was found to be 100 parts by weight. In addition, the content of the polyvinyl alcohol and the content of the glycerin in the aqueous phase were found to be 27.1% by weight and 10.9% by weight, respectively. The average particle size of the aqueous phase was determined to be 1.2 µm. The resulting oily composition was inspected for the storage stability according to the same procedures used in Example 1. The evaluation results thus obtained are listed in Table 10.

Comparative Example 20

The same procedures used in Example 14 were repeated to give a W/O type emulsion. Then the W/O type emulsion was (hied using an oil pump for a time shorter than that used in Example 14 to give a liquid white codeine phosphate-containing oily composition, whose water content was greater than that observed in Example 14. The water content of the oily composition was found to be 6.3% by weight. The water content and the codeine phosphate content of the aqueous phase dispersed in the oil phase were found to be 33.3% by weight and 19.1% by weight, respectively. Moreover, the amount of the pullulan relative to 100 parts by weight of the codeine phosphate was found to be 200 parts by weight. In addition, the content of the pullulan and the content of the glycerin in the aqueous phase were found to be 38.1% by weight and 9.5% by weight, respectively. The average particle size of the aqueous phase was determined to be 0.8 µm. The resulting oily composition was inspected for the storage stability according to the same procedures used in Example 1. The evaluation results thus obtained are listed in Table 10.

Comparative Example 21

An aqueous phase was prepared by mixing 80.0 g of Sunphenone, 20.0 g of CELL ACE#40, 20.0 g of Sorbit L-70 and 450.0 g of a 20% by weight aqueous ethanol solution and then heated to 60° C. On the other hand, an oil phase was prepared by mixing 400.0 g of soybean oil, 28.0 g of SY GLYSTAR CR-310 and 2.0 g of EMULGY MU and then dissolved with heating at 60° C. To the oil phase, there was slowly added the oil phase, followed by emulsification through stirring with a spatula for 20 minutes. After the emulsification, the resulting emulsion was dried under reduced pressure using an oil pump to give a liquid brown tea extract-containing oily composition. The aqueous ethanol solution content of the oily composition was found to be 0.1% by weight. The aqueous ethanol solution content and the tea extract content of the solid phase dispersed in the oil phase were found to be 0.5% by weight and 69.8% by weight, respectively. Moreover, the amount of the corn fibers relative to 100 parts by weight of the tea extract was found to be 25.0 parts by weight. In addition, the content of the corn fibers and the sorbit content in the solid phase were found to be 17.5% by weight and 12.2% by weight, respectively. The average particle size of the solid phase was determined to be 6.7 µm. The resulting oily composition was inspected for the storage stability according to the same procedures used in Example 1. The evaluation results thus obtained are listed in Table 10.

TABLE 8

Results of Storage Stability Evaluation

| Example No. | | 9 | 10 | 11 | 12 | 13 | 14 |
|---|---|---|---|---|---|---|---|
| Immediately After Preparation | | ◎ | ◎ | ◎ | ◎ | ◎ | ◎ |
| 5° C. | one month | ◎ | ◎ | ◎ | ◎ | ◎ | ◎ |
| | three months | ◎ | ◎ | ◎ | ◎ | ◎ | ◎ |
| | six months | ◎ | ◎ | ◎ | ◎ | ◎ | ◎ |
| Room Temp. | one month | ◎ | ◎ | ◎ | ◎ | ◎ | ◎ |
| | three months | ◎ | ◎ | ◎ | ◎ | ◎ | ◎ |
| | six months | ◎ | ◎ | ◎ | ◎ | ◎ | ◎ |
| 40° C. | one month | ◎ | ◎ | ◎ | ◎ | ◎ | ◎ |
| | three months | ◎ | ◎ | ◎ | ◎ | ◎ | ◎ |
| | six months | ◎ | ◎ | ◎ | ◎ | ◎ | ◎ |

TABLE 9

Results of Storage Stability Evaluation

| Comparative Example No. | | 14 | 15 | 16 | 17 |
|---|---|---|---|---|---|
| Immediately After Preparation | | ◎ | ◎ | ◎ | ◎ |
| 5° C. | one month | ○ | ○ | ○ | ○ |
| | three months | ○□X | ○□ | ○□ | ○□ |
| | six months | ▲■X | △□ | △□ | △□ |
| Room Temp. | one month | ○□X | ○□ | ○□ | ○□ |
| | three months | ▲■X | △□ | △□ | △□ |
| | six months | ▲■X | ▲■X | ▲■X | ▲■X |
| 40° C. | one month | ▲■X | △□ | △□ | △□ |
| | three months | ▲■X | ▲■X | ▲■X | ▲■X |
| | six months | ▲■X | ▲■X | ▲■X | ▲■X |

TABLE 10

Result of Storage Stability Evaluation

| Comparative Example No. | | 18 | 19 | 20 | 21 |
|---|---|---|---|---|---|
| Immediately After Preparation | | ◎ | ◎ | ◎ | ○ |
| 5° C. | one month | ○ | ○ | ○ | △□ |
| | three months | ○□ | ○□ | ○□ | ▲■ |
| | six months | △□ | △□ | △□ | ▲■ |

TABLE 10-continued

Result of Storage Stability Evaluation

| Comparative Example No. | | 18 | 19 | 20 | 21 |
|---|---|---|---|---|---|
| Room Temp. | one month | ○□ | ○□ | ○□ | Δ■ |
| | three months | Δ□ | Δ□ | Δ□ | Δ■ |
| | six months | Δ■X | Δ■X | Δ■X | Δ■ |
| 40° C. | one month | Δ□ | Δ□ | Δ□ | Δ■ |
| | three months | Δ■X | Δ■X | Δ■X | Δ■ |
| | six months | Δ■X | Δ■X | Δ■X | Δ■ |

[Confirmation of Taste-Masking Effect]

Various kinds of the oily compositions and emulsified compositions containing aqueous effective substances and prepared in Examples 8 to 10, 12 and 13 and Comparative Examples 14 to 21 were inspected for the taste-masking effect thereof by getting 20 normal persons to eat them and to judge whether they could be conscious of the taste of the aqueous effective substances or not. The results thus obtained are summarized in the following Table 11.

TABLE 11

Results of Sensory Test (number of persons)

| Ex. No. | 8 | 9 | 10 | 12 | 13 | 14* | 15* | 16* | 17* | 18* | 19* | 20* | 21* |
|---|---|---|---|---|---|---|---|---|---|---|---|---|---|
| ○ | 20 | 17 | 19 | 20 | 20 | 0 | 0 | 0 | 0 | 0 | 0 | 0 | 0 |
| Δ | 0 | 3 | 1 | 0 | 0 | 0 | 0 | 0 | 0 | 0 | 0 | 0 | 0 |
| X | 0 | 0 | 0 | 0 | 0 | 20 | 20 | 20 | 20 | 20 | 20 | 20 | 20 |

*Comparative Example
○: The panelists were not conscious of the taste of the aqueous effective substance.
Δ: The panelists were slightly conscious of the taste of the aqueous effective substance.
X: The panelists were conscious of the taste of the aqueous effective substance.

EFFECTS OF THE INVENTION

As has been described above in detail, the oily composition of the present invention comprises an oil phase and a solid phase dispersed in the oil phase in a fine particulate state and the water content or the aqueous alcohol solution content is not more than 30% by weight. Therefore, the composition permits the lightening of the taste peculiar to an aqueous effective substance, it hardly causes any precipitation of the aqueous effective substance even if the composition is stored over a long time period or it has excellent storage stability. In addition, the method according to the present invention permits the preparation of an oily composition having excellent storage stability.

Moreover, the oily composition of the present invention can be used in foods, feeds and medicines because of its ability of lightening the taste of an aqueous effective substance and its excellent storage stability. Further the composition permits the use of an aqueous effective substance in the form of an oily dispersion and therefore, the composition can be used in the fields of agriculture and other various industrial fields such as mechanics.

What is claimed is:

1. An oily composition comprising a solid phase containing an effective substance soluble in water and/or in an aqueous alcohol solution and an oil phase containing an oily component and an emulsifying agent having an HLB value of not more than 10, wherein the solid phase is dispersed in the oil phase in the form of a fine particulate state having an average particle size of not more than 5 $\mu$m and the water content or the aqueous alcohol solution content of the solid phase is not more than 20% by weight.

2. The oily composition of claim 1 wherein the effective substance soluble in water and/or in an aqueous alcohol solution is selected from the group consisting of colorants, enzymes, bacteria, antioxidants, biologically active substances, preservatives and bitter substances.

3. The oily composition of claim 1 which comprises a polyhydric alcohol in an amount ranging from 1 to 40% by weight based on the total weight of the solid phase.

4. The oily composition of claim 1 wherein the solid phase comprises an emulsifying agent having an HLB value of not less than 10.

5. The oily composition of claim 1 wherein the oil phase comprises an oil-soluble effective substance.

6. The oily composition of claim 1 which comprises 5 to 75% by weight of the solid phase and 95 to 25% by weight of the oil phase.

7. An oily composition comprising a solid phase containing an effective substance soluble in water and/or in an aqueous alcohol solution and a film-forming agent in an amount ranging from 1 to 2000 parts by weight per 100 parts by weight of the effective substance; and an oil phase containing an oily component and an emulsifying agent having an HLB value of not more than 10, wherein the solid phase is dispersed in the oil phase in the form of a fine particulate state having an average particle size of not more than 5 $\mu$m and the water content of the solid phase is not more than 20% by weight.

8. The oily composition of claim 7 wherein the effective substance soluble in water and/or in an aqueous alcohol solution is selected from the group consisting of colorants, enzymes, bacteria, antioxidants, biologically active substances, preservatives and bitter substances.

9. The oily composition of claim 7 which comprises a polyhydric alcohol in an amount ranging from 1 to 40% by weight based on the total weight of the solid phase.

10. The oily composition of claim 7 wherein the film-forming agent is gelatin or gum arabic.

11. The oily composition of claim 7 wherein the film-forming agent is glue, a culture obtained by treating starch with microorganisms, hemicellulose or a water-soluble film-forming synthetic polymer.

12. The oily composition of claim 7 wherein the solid phase comprises an emulsifying agent having an HLB value of not less than 10.

13. The oily composition of claim 7 wherein the oil phase comprises an oil-soluble effective substance.

14. The oily composition of claim 7 which comprises 5 to 75% by weight of the solid phase and 95 to 25% by weight of the oil phase.

15. A method for preparing an oily composition comprising a solid phase containing an effective substance soluble in water and/or in an aqueous alcohol solution and an oil phase containing an oily component and an emulsifying agent having an HLB value of not more than 10, wherein the solid phase is dispersed in the oil phase in the form of a fine particulate state having an average particle size of not more than 5 µm and the water content or the aqueous alcohol solution content of the solid phase is not more than 20% by weight, the method comprising the steps of emulsifying an aqueous phase containing an effective substance soluble in water and/or in an aqueous alcohol solution, a water-soluble film-forming agent and water or an aqueous alcohol solution with an oil phase containing an oily component and an emulsifying agent to form a W/O type emulsion and then drying the W/O type emulsion.

16. The method of claim 15 wherein the aqueous phase comprises a polyhydric alcohol.

* * * * *